United States Patent
Teshima

Patent Number: 5,471,553
Date of Patent: Nov. 28, 1995

[54] MULTICORE HOLLOW OPTICAL FIBER AND A METHOD FOR PREPARATION THEREOF

[75] Inventor: Shinichi Teshima, Yokohama, Japan

[73] Assignee: Asahi Kasei Kogyo Kabushiki Kaisha, Osaka, Japan

[21] Appl. No.: 30,425

[22] PCT Filed: Sep. 30, 1992

[86] PCT No.: PCT/JP92/01260

§ 371 Date: Mar. 23, 1993

§ 102(e) Date: Mar. 23, 1993

[51] Int. Cl.$^6$ ................................. G02B 6/20
[52] U.S. Cl. .................. 385/125; 385/115; 385/126; 65/393; 65/401
[58] Field of Search ............................ 385/125, 126, 385/115, 117, 120, 121, 122, 123, 124; 65/393, 401

[56] References Cited

U.S. PATENT DOCUMENTS

| | | | |
|---|---|---|---|
| 3,556,635 | 1/1971 | Schrenk et al. | 385/125 X |
| 3,823,996 | 6/1974 | Kompfer et al. | 385/115 |
| 3,902,880 | 9/1975 | Strack et al. | 785/115 |
| 4,768,857 | 9/1988 | Sakunaga et al. | 385/115 |
| 4,805,987 | 2/1988 | Laakmann et al. | 385/125 |
| 4,806,289 | 2/1989 | Laursen et al. | 385/125 X |
| 4,812,012 | 3/1989 | Terada et al. | 385/115 |
| 4,842,365 | 6/1989 | Terada et al. | 385/115 |
| 4,872,740 | 10/1989 | Terada et al. | 385/117 |
| 5,155,792 | 10/1992 | Vali et al. | 385/125 |
| 5,221,308 | 6/1993 | Krohn et al. | 385/125 |
| 5,297,226 | 3/1994 | Fukunishi | 385/115 X |

FOREIGN PATENT DOCUMENTS

| | | | |
|---|---|---|---|
| 0207705 | 1/1987 | European Pat. Off. . | |
| 0443854 | 8/1991 | European Pat. Off. . | |
| 44-21176 | 9/1969 | Japan | 385/115 |
| 56-39505 | 7/1974 | Japan . | |
| 54-116417 | 9/1979 | Japan . | |
| 55-133003 | 10/1980 | Japan . | |
| 61-109418 | 7/1986 | Japan | 385/115 |
| 62-3206 | 1/1987 | Japan | 385/115 |
| 62-75603 | 4/1987 | Japan | 385/115 |
| 2-176605 | 7/1990 | Japan | 385/115 |
| 3-197904 | 8/1991 | Japan | 385/115 |
| WO88/05381 | 7/1988 | WIPO . | |

*Primary Examiner*—John D. Lee
*Assistant Examiner*—Phan T. H. Palmer
*Attorney, Agent, or Firm*—Pennie & Edmonds

[57] ABSTRACT

The present invention relates to a multicore hollow optical fiber comprising a hollow central part and a plastic peripheral part, more particularly, a multicore hollow optical fiber having a cross-section of the peripheral part wherein (a) an islands-in-sea structure is formed; (b) the islands comprise a core resin having at least higher refractive index than a cladding resin; (c) the sea comprises a cladding resin or the third resin; (d) the core resin is surrounded by the cladding resin; and (e) voids do not substantially exist; and also having, in the direction of the axis, the above cross-section continuously from one end to the other.

10 Claims, 8 Drawing Sheets

MULTICORE HOLLOW OPTICAL FIBER AND A METHOD FOR PREPARATION THEREOF

Technical Field

The present invention relates to a multicore hollow optical fiber and a method for preparation thereof. More particularly, this invention is concerned with a multicore hollow optical fiber which can be used for a compact endoscope and an optical sensor in medical and measuring industries by arranging, in its hollow, an image optical fiber, a single optical fiber, optical parts such as a lens, an electric cord, electric parts such as an electrode and an electron element, fluid such as gas and liquid, a chemical reaction material and the like; and also with a method for preparation thereof.

Background Art

U.S. Pat. No. 4,806,289 discloses a hollow optical fiber comprising a hollow central part and a peripheral part wherein the first layer is a cladding layer; the second layer is a core layer; and the third layer is a cladding layer, as shown in FIG. 11 of the present specification. The hollow optical fiber is stiff and does not have bending properties because of its layer structure. Accordingly, the hollow optical fiber easily buckles by bending and it easily breaks by cracking. Further, a fiber is not easily inserted into the hollow part of the hollow optical fiber because the hollow optical fiber has low elasticity.

Japanese Patent Publication No. 211761/1969 proposes a method for preparing a multicore hollow optical fiber wherein many optical fibers 20 are arranged around stem 19 in the layer to form a fiber bundle as shown in FIG. 12 of the present specification. The fiber bundle is heated to soften the optical fibers and to fusion-bond the outer layer, and then it is wound up while drawing. In this specification, there is no description in regard to the quality of the optical fiber. However, when a plastic optical fiber is prepared according to the above-mentioned method, voids remain between each optical fiber even if the resultant fiber bundle is heated so as to completely fusion-bond each optical fiber. Therefore, a multicore hollow optical fiber obtained by this method is easily taken into pieces by bending. Further, light cannot easily pass through the fiber since the cladding and core resins are mixed up. Accordingly, there cannot be obtained a high quality multicore hollow optical fiber suitable for a medical endoscope, of which fibers have a high accuracy in a bore or an outside diameter of the hollow over one to several meters in length and do not unnaturally bend or break by bending. Further, this method for preparing the fiber has a shortcoming in high cost caused by its complicated producing steps.

On the other hand, U.S. Pat. No. 3,556,635 discloses a multicore plastic fiber having an islands-in-sea structure wherein a core resin constitutes islands and a cladding resin constitutes a sea. The multicore plastic fiber is obtained by extruding the melted core and cladding resins with a composite spinning die. However, this patent does not contain a description about a multicore hollow optical fiber. Also, a multicore hollow optical fiber obtained according to the above method has not yet been attained.

In Japanese Utility Model Application Laid-Open No. 109418/1986, an endoscope is disclosed as shown in FIGS. 13, 14A and 14B of the present specification. The endoscope comprises image fiber 14, cylindrical part 22, and a body. Cylindrical part 22 has image fiber 14 in its hollow and has a plurality of optical fibers 20 in its wall composed of molding compound 21. A part of cylindrical part 22, image fiber 14 and light guide 23 bundling a plurality of optical fibers 20 are coated with resin 25, and they form the body. However, the endoscope is not compact enough because of the difference in diameters between cylindrical portion 22 and the body. This difference is caused by the structure of the endoscope, that is, the endoscope comprises cylindrical portion 22 and light guide 23 which are coated with resin 25. The method for making the edge of light guide 23 bundling a plurality of optical fibers to the above-mentioned structure requires a long and complicated step to fabricate light guide 23. Therefore, it is very difficult to manufacture an endoscope requiring high accuracy.

DISCLOSURE INVENTION

The present invention provides an optical fiber comprising a hollow central part and a plastic peripheral part, wherein a cross-section of the peripheral part of the multicore hollow optical fiber has (a) an islands-in-sea structure; (b) islands comprising a core resin having at least higher refractive index than a cladding resin; (c) a sea comprising the cladding resin or a third resin; (d) a core resin surrounded by the cladding resin; and (e) no substantial voids; and also the multicore hollow optical fiber having, in the direction of the axis, approximately the same cross-section of the peripheral part continuously from one end to the other end of the multicore hollow optical fiber.

The term "an islands-in-sea structure" in the present invention indicates a structure comprising islands of core resin 1 and a sea of cladding resin 2 as shown in FIG. 1 and also indicates a structure having islands comprising core resin 1 surrounded by cladding resin 2 in a concentric configuration and a sea of third resin 4 as shown in FIG. 2.

The multicore hollow optical fiber of the present invention has a hollow in the central part. The hollow may be formed near the center of the optical fiber. When the optical fiber has a circular cross-section, it is preferred that the hollow and the peripheral part are a concentric configuration, i.e., the hollow and the peripheral part have the same center. In this case, the outside and inside diameters of the multicore hollow optical fiber of the present invention can be controlled as desired. The preferred fiber has an outside diameter of 0.1 to 5.0 mm and an inside diameter of 0.05 to 4.0 mm since such a fiber is easy to produce. Further, the fiber can be extruded, if necessary, to be about 1.1 to 3 times its original length in order to improve the mechanical strength.

The multicore hollow optical fiber of the present invention has an islands-in-sea structure wherein many minute islands exist in the cross-section of the peripheral part. The number of islands is preferably more than 100, more preferably 200 to 10,000. The fiber characteristically has a smooth wall surface because of the number of islands, so that the fiber can be smoothly bended. It is preferable that the multicore hollow optical fiber constitutes a structure wherein islands of minute cores are piled up, in the direction of the radius, in several layers for maintaining the mechanical strength and attaining a light uniformity and intensity. The number of the islands in the direction of the radius is preferably 2 or more, more preferably 3 or more.

The islands are surrounded by the sea comprising a cladding resin or the third resin, and there is substantially no viods around the islands. Accordingly, the multicore hollow optical fiber of the present invention has no problem that cracks may occur from voids due to repeated bending.

Any island shape is acceptable but a preferable shape is round.

The fiber having a larger core area in cross-section is suitable for use in a light guide. The preferable core area is from 50 to 95% based on the cross-section area. When the ratio of the core area is high, it is advantageous that the optical path area becomes large and bright. However, when the sea area is too small, the strength of the multicore hollow optical fiber unpreferably decreases. For the core resin of the multicore hollow optical fiber of the present invention, a resin known as the core resin of the plastic optical fiber can be employed. For example, a single polymer and a copolymer of methyl methacrylate (hereinafter referred to as a MMA resin), polycarbonate, a styrene resin and the like can be employed. The preferred resin has a melt flow index of between about 0.1 g/10 min. and about 100 g/10 min. at a loading of 3.8 kg at a temperature of 230° C. according to ASTM-1238. Among MMA resins, a resin having a melt flow index of from 0.5 g/10 min. to 3 g/10 min. is particularly preferable.

For the cladding resin, a resin conventionally used for a plastic optical fiber can also be employed. The refractive index of the cladding resin is preferably smaller than that of the core resin by 0.02 or more, more preferably by 0.08 or more. Concerning the flowability of the cladding resin at the time of melting, a resin having relatively high flowability is preferable. The cladding resin has preferably a melt flow index of from 5 g/10 min. to 200 g/10 min., more preferably 10 g/10 min. or more, at a loading of 3.8 kg at a temperature of 230° C. according to ASTM-1238. Further, the cladding resin having high flowability is acceptable.

For the third resin, a resin can be selected according to the desire, i.e., a resin having flexibility and high mechanical strength, a resin having no light transmission properties to shield a leakage of light from adjacent islands, a resin having no interaction with blood in view of medical use, and the like.

The third resin includes, for example, a vinylidene fluoride type resin such as a copolymer of vinylidene fluoride and tetrafluoroethylene, a copolymer of vinylidene fluoride and hexafluoropropene, a terpolymer of vinylidene fluoride, tetrafluoroethylene and hexafluoropropene; a copolymer of ethylene and vinyl acetate; polyethylene; polyvinyl chloride; a copolymer of ethylene and vinyl alcohol; resins having light shielding properties obtained by adding additives such as carbon to the above listed resins; and the like. A melt flow index of these resins is preferably as high as or higher than that of the cladding resin so that these resins can be formed together with the core and cladding resins by melt composite spinning.

The most preferred combination of the core and cladding resins is a MMA resin for the core resin and a vinylidene fluoride type resin for the cladding resin. As a vinylidene fluoride type resin, for example, a copolymer of vinylidene fluoride and tetra-fluoroethylene, wherein the ratio of vinylidene fluoride units is in the range of from 60 to 99% by mole, preferably from 78 to 86% by mole, is used. Also, a copolymer of vinylidene fluoride and hexafluoropropene, a terpolymer of vinylidene fluoride, tetrafluoroethylene and hexafluoropropene, a terpolymer of vinylidene fluoride, trifluoroethylene and hexafluoroacetone, and the like can be used. Since these vinylidene fluoride type resins have good compatibility with a MMA resin forming the core, the mechanical strength of the obtained multicore hollow optical fiber is high. When a MMA resin is used as the core resin, besides the vinylidene fluoride type resin as the cladding resin, a fluoro-alkylmethacrylate resin, an α-fluoroalkylmethacrylate resin and a generally known resin as a cladding resin of the plastic optical fiber can be used. When a styrene type resin is used as the core resin, a MMA resin, a copolymer of ethylene and vinyl acetate and the like are preferably used as the cladding resin. When polycarbonate is used as the core resin, a MMA type resin, a vinylidene fluororide type resin, a 4-methylpentene-1 resin, a copolymer of ehtylene and vinyl acetate and the like are used as the cladding resin.

For obtaining the multicore hollow optical fiber of the present invention, the melted core resin and the melted cladding resin, and if necessary, the melted third resin are initially fed to a composite spinning die. Then, the melted core resin is extruded from the die plate having a number of holes to form a number of linear cores. The melted cladding resin is extruded around the resulting linear cores to form an islands-in-sea structure wherein the core constitutes islands and the cladding constitutes a sea in the cross-section. If the third resin is employed, the melted third resin is extruded around the linear core obtained by extruding the melted cladding resin so as to surround the linear cores of the core resin to form an islands-in-sea structure wherein the core and the cladding constitute islands and the third resin constitutes a sea in the cross-section. A fluid is introduced into the central part of the islands-in-sea structure to form a hollow. The preferable fluid is gas such as nitrogen gas and air. In some cases, a resin which is, for example, capable of being washed away with water or being dissolved in an organic solvent after it is formed is also acceptable.

FIG. 3 shows an example of a composite spinning die suitable for producing the multicore hollow optical fiber of the present invention. The melted core resin is fed from core resin supply port 5. The melted cladding resin is fed from cladding resin supply port 6. Gas such as air, nitrogen gas or the like is fed from gas supply port 7. Die plates A 8 and B 9 are used in forming the islands of the core resin and charging the cladding resin around the islands, respectively. Holes of these plates can be arranged at the vertices of a equilateral triangle, at the four corners of a square, or in regular concentric configuration from the center of the hollow. Also, the hole arrangement not having a strict regularity is acceptable if holes are arranged almost uniformly on a plate.

The resin from die plate B 9 is extruded along casing 10 whose pointed end is made smaller by fitting a taper. The structure of die plate B 9 is such that holes are arranged so as to extrude microscopic cores wherein the obtained multicore hollow optical fiber has approximately a desired ratio of the outside diameter to the inside diameter. Taper nozzle 11 having preferably the shape which becomes gradually smaller from the exit of die plate B 9 toward the exit of the casing, is arranged at the place where the hollow of the central part is formed. Gas, introduced from gas supply port 7, passes or drifts in taper nozzle 11. Taper nozzle 11 and casing 10 are preferably arranged so that a ratio of the inside diameter of the casing to that of the taper nozzle may become a desired ratio of the outside diameter to the inside diameter of the multicore hollow optical fiber.

Taper nozzle 11 is preferably arranged such that the pointed ends of taper nozzle 11 and casing 10 are approximately on the same plane so as to stably obtain the desired multicore hollow optical fiber. By arranging taper nozzle 11 as mentioned above, the multicore hollow optical fiber is formed in a similar pattern to the structure of the die plate.

The multicore hollow optical fiber of the present invention is obtained by drawing the melted resin having a hollow formed by the above method so as to have the desired diameter while cooling.

FIG. 5 shows a composite spinning die to be used when the third resin is employed. Die plate C 13 is further incorporated behind die plate B 9. Pairs of larger and smaller pipes having the common center are respectively placed from die plates A 8 and B 9 so as to go into holes of die plate C 13. The core resin is introduced into the inner pipe, and the cladding resin is introduced between the inner and outer pipes. Further, the third resin can be introduced from third resin supply port 12, i.e., between die plates B 9 and C 13 so as to surround the cladding resin.

The multicore hollow optical fiber of the present invention can be mainly used for a compact light guide. Further, since the multicore hollow optical fiber of the present invention characteristically has high flexibility, high resistance to bending and durability, it is advantageously used for medical and measurment uses and the like. The multicore hollow optical fiber of the present invention has high flexibility such that its shape becomes oval by pushing when it is concentrically produced, but its shape is easily restored to a circle when the transformed multicore hollow optical fiber is pushed in the direction of the major axis. Therefore, it is easy to introduce an image fiber, which is made of glass and plastics, into the hollow part. The concentrically produced optical fiber is not broken when it is used after its pointed end is transformed to the shape such as an oval other than a circle. Therefore, the present optical fiber can be used in any shape depending on the desired use. Also, it can be configurated in any shape other than a concentric figure depending on the desired use.

The multicore hollow optical fiber of the present invention can be also used for a light guide having the property of an image fiber, since the arrangement of each island in the end face of the fiber is continuously kept in the direction of the axis of the fiber. The cores of the multicore optical fiber of the present invention are in parallel with each other and never cross, so that islands in the both ends are symmetrical to the vertical plane of the fiber. Using this property, in addition to a light source, a laser beam having a diameter of several to 30 μm or a light having different wavelength from the light source can be supplied to one end of the fiber and then can be transmitted to the relevant points at the other end. Also, the light intensity of the irradiated light is able to be adjusted. Thus, the multicore hollow optical fiber of the present invention can provide a precise method of lighting which has not been attained by the prior art.

A light guide for a compact endoscope and an optical fiber sensor in the field of medical and industrial use are important applications of the multicore hollow optical fiber of the present invention. When used in an endoscope, as shown in FIG. 10, object lens 17 is arranged in the hollow at one end of the multicore hollow optical fiber, and an image fiber is put in the hollow so as to attach an end of the image fiber to the object lens. If the other end of the image fiber is taken out from the light guide, i.e., the multicore hollow optical fiber, a hole may be made in the middle of the multicore hollow optical fiber to take out the image fiber. Such hole may be made by a gimlet, a heated needle, a laser beam or the like. Instead of making a hole, the end or the middle of the multicore hollow optical fiber may be cut. Also, the fiber in the hollow part may be taken out from the hole of the multicore hollow optical fiber so that the fiber and the multicore hollow optical fiber may be connected to a light detector and a light source, respectively.

Multicore hollow optical fibers which is capable of being readily torn are composed of an elastic core resin and an elastic cladding resin, for example, polycarbonate as a core resin and a copolymer of ethylene vinyl acetate as a cladding resin. Multicore hollow fibers composing of MMA resin cores and vinylidene fluoride resin claddings are relatively easy to tear. Image fibers which can be used for the present invention include thin quartz glass fibers having 1,000 to 200,000 picture elements and plastic fibers having 1,000 to 10,000 picture elements.

When the optical fiber of the present invention is used in an optical fiber sensor, for example, a reflex optical fiber sensor is prepared by introducing a single optical fiber into the hollow at one end of the multicore hollow optical fiber. The reflex optical fiber sensor detects an object by receiving the reflected light, which is emitted from one end of the multicore hollow optical fiber, through the single optical fiber. By using the multicore hollow optical fiber of the present invention, the sensor can be made up compactly.

Furthermore, the multicore hollow optical fibers of the present invention can be used for an optical fiber probe by feeding gas or liquid chemicals into the hollow or by fitting electron elements or electric wires etc. into the hollow. This optical fiber probe has functions as an optical fiber sensor. That is, the ends of this optical fiber probe are active, so that luminous phenomenon are produced by chemical reactions or physical responses at the end of the probe, and then the optical effect can be detected.

The multicore hollow optical fiber can be used as it is or for medical treatment after covering the outside of the fiber with resins compatible to a living body so as to make the outside harmless. To improve mechanical strength or chemical resistance, the outside of the fiber may be covered with other resins. Those resins include fluoro plastics such as silicone plastics and teflon plastics, a resin containing an ethylene and vinyl alcohol, polyethylene plastics, ethylene chloride plastics, polyurethane plastics and the like.

DESCRIPTION OF SYMBOLS

Figure 1:
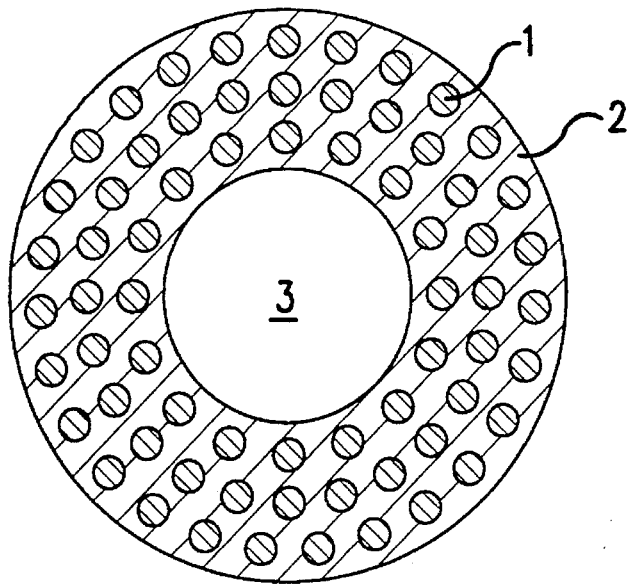
FIG. 1 is a cross-section view of a multicore hollow optical fiber of the present invention.
Figure 2:
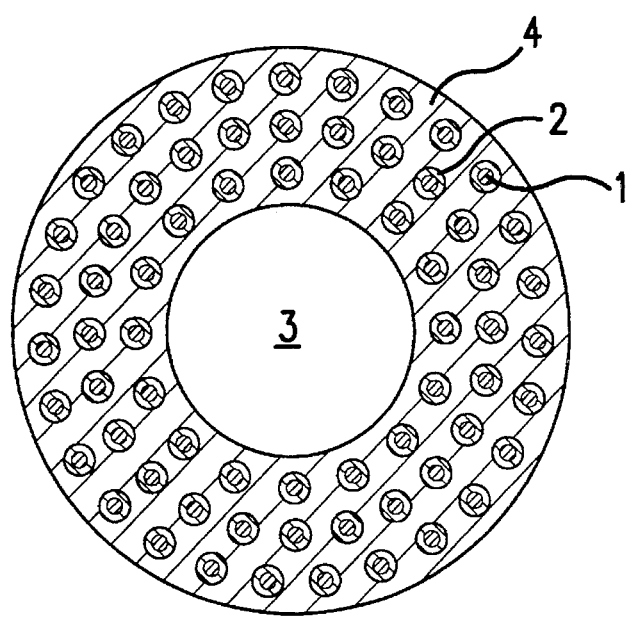
FIG. 2 is a cross-section view of another multicore hollow optical fiber of the present invention.

1: core resin
2: cladding resin
3: hollow part
4: third resin
5: core resin supply port
6: cladding resin supply port
7: gas supply port
8: die plate A
9: die plate B
10: casing
11: taper nozzle
12: third resin supply port
13: die plate C
14: image fiber
15: eye lens
16: light source
17: object lens
18: multicore hollow optical fiber
19: stem
20: optical fiber
21: molding compound
22: cylidrical portion
23: light guide
24: combination lens system
25: coating resin
26: hollow part

BEST MODE FOR CARRYING OUT THE INVENTION

The present invention is now illustrated in detail by following Examples.

[EXAMPLE 1]

Figure 3:
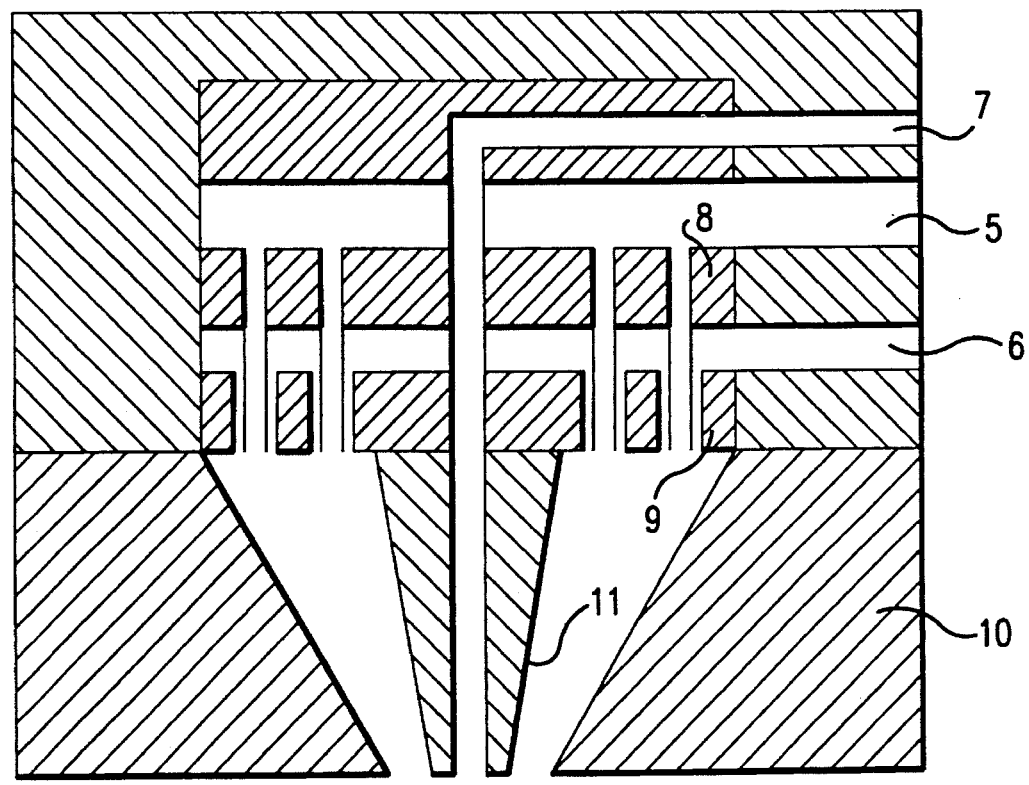
FIG. 3 is a cross-section view of the first composite spinning die for a multicore hollow optical fiber of the present invention.

As a core resin, a MMA resin having a melt flow index of 1.5 g/10 min. at a loading of 3.8 kg at a temperature of 230° C. according to ASTM-1238, and a refractive index of 1.49 was employed. This resin comprised 99.5% by weight of methyl methacrylate (MMA) unit and 0.5% by weight of methyl acrylate (MA) unit. As a cladding resin, a resin having a molar ratio of a vinylidene fluoride unit to a trifluoroethylene unit to a hexafluoroacetone unit of 80:14:6, a melt flow index of 35 g/10 min. and a refractive index of 1.40 was employed. The composite spinning die shown in FIG. 3 was employed, the die plate of which had 1,000 holes. First, a linear core was formed by extruding the core resin. Second, the obtained linear core was coated with the cladding resin. At this time, the die was heated to 230° C.; the melted core resin and the melted cladding resin were respectively fed at 0.85 kg/hr., 0.15 kg/hr.; and nitrogen gas was fed under atmospheric pressure into the nozzle. A hollow melted strand having an islands-in-sea structure was obtained from the exit of the die. The resultant hollow melted strand was drawn to obtain a multicore optical hollow fiber having an outside diameter of 1.0 mm and an inside diameter of 0.5 mm. The resultant multicore hollow optical fiber has an islands-in-sea structure in cross-section as shown in FIG. 1 wherein the area ratio of the islands was 89.5%. The fiber was capable of transmitting room light even when it was 15 meters in length. As a result, it was confirmed that the resultant fiber was advantageously used as a light guide for a short distance, i.e., a few meters.

[EXAMPLE 2]

A multicore optical hollow fiber having an outside diameter of 1.0 mm and an inside diameter of 0.65 mm was obtained in the same manner as in Example 1, except that polycarbonate having a molecular amount of 15,000 and a refractive index of 1.59 was used as a core resin, and an ethylene-vinyl acetate copolymer having a refractive index of 1.49 and ratio of vinyl acetate unit of 25% by weight was used as a cladding resin. The resultant multicore hollow optical fiber had an islands-in-sea structure in cross-section as in Example 1 wherein the area ratio of the islands was 81.5%. The fiber was capable of transmitting room light even when it was 5 meters in length.

The resultant multicore hollow optical fiber was easily torn lengthwise. Therefore, an image fiber and the like were easily inserted into the hollow part by making a cut in a part of the multicore optical hollow fiber.

[EXAMPLE 3]

Figure 4:
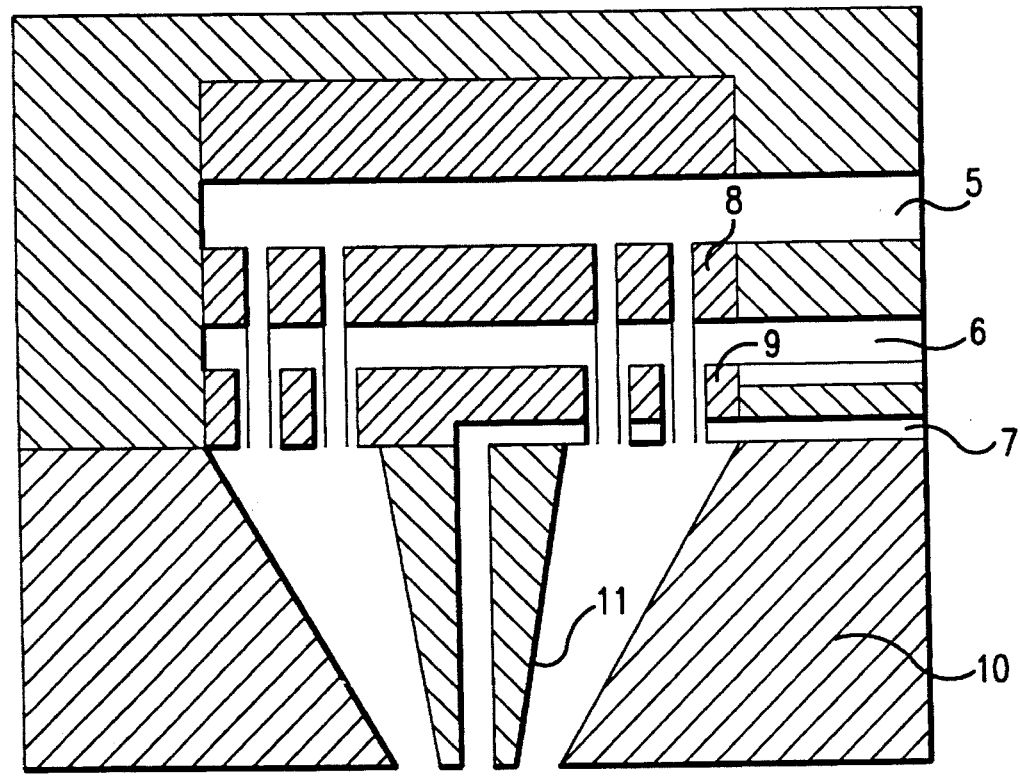
FIG. 4 is a cross-section view of the second composite spinning die for a multicore hollow optical fiber of the present invention.
Figure 5:
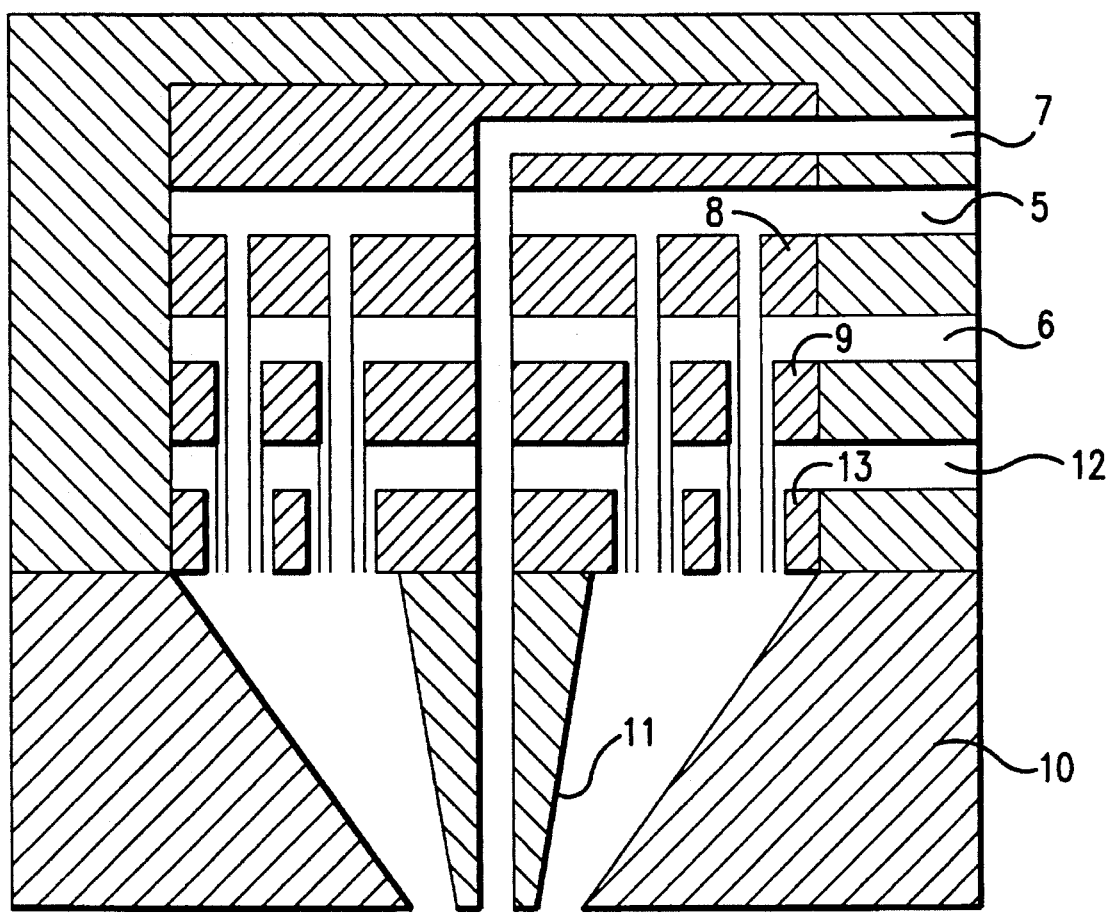
FIG. 5 is a cross-section view of the third composite spinning die for a multicore optical hollow fiber of the present invention.
Figure 6:
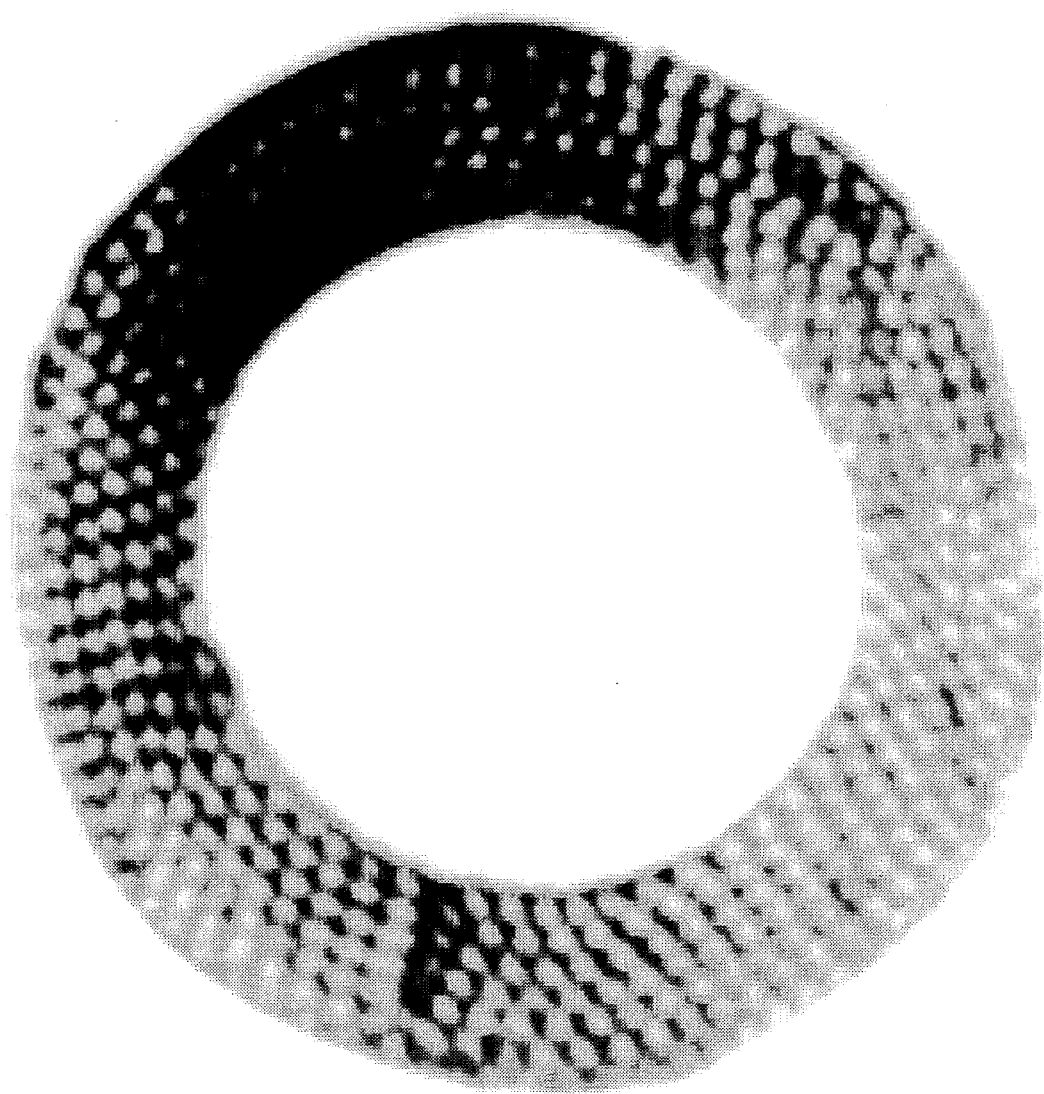
FIG. 6 is a photomicrograph of a cross-section view of the multicore optical hollow fiber obtained in Example 3.
Figure 7A:
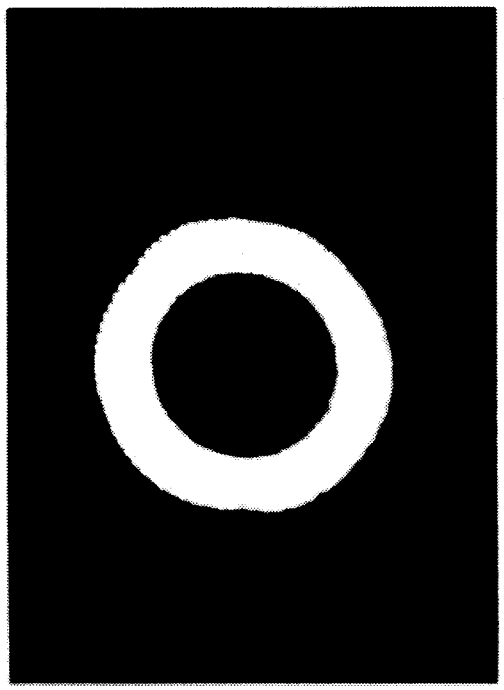
FIGS. 7A to 7D are photographs of light pattern given by a light guide, which is composed of the multicore hollow optical fiber obtained in Example 3.
Figure 7B:
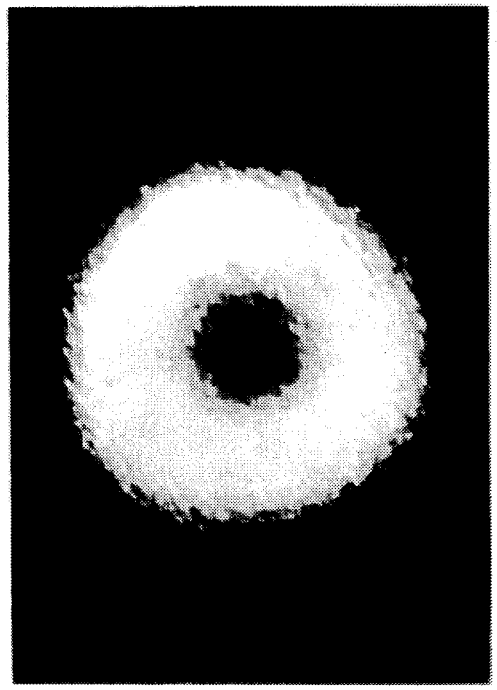
Figure 7C:
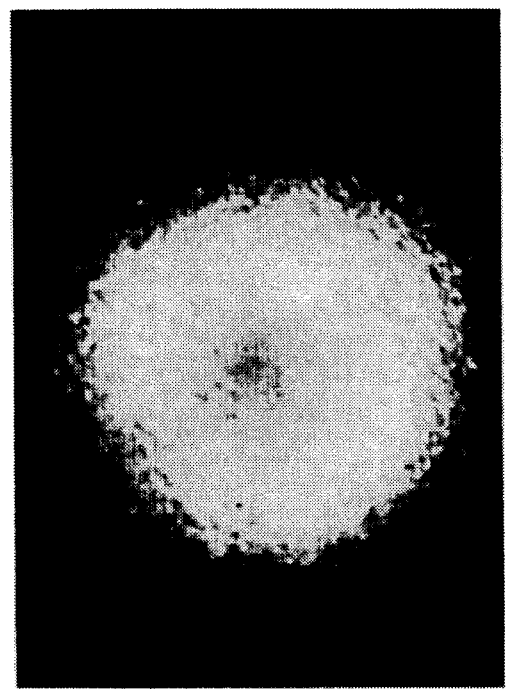
Figure 7D:
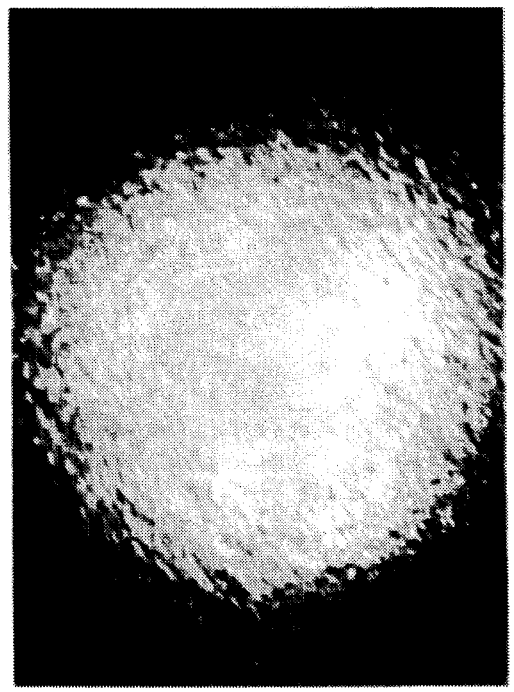

As a core resin, a MMA resin having a melt flow index of 1.5 g/10 min. at a loading of 3.8 kg at 230° C. according to ASTM-1238 was employed. This resin comprised 99.5% by weight of MMA unit and 0.5% by weight of MA unit. As a cladding resin, a resin having a molar ratio of a vinylidene fluororide unit to a tetrafluoroethylene unit of 81:19, a melt flow index of 30 g/10 min. and a refractive index of 1.40 was employed. A composite spinning die shown in FIG. 4 was employed. A linear passage to introduce gas is arranged in the radial direction. This structure was simpler than the structure of the composite spinning die in Example 1. A conic nozzle for introducing nitrogen gas and forming a hollow was arranged in the central part of the die, and a plate having 500 holes was arranged around the nozzle. Linear cores were formed by extruding the core resin on the plate, then the obtained linear cores were coated with the cladding resin. At this time, the die was heated to 230° C.; the melted core resin and the melted cladding resin were fed at 462 ml/hr. and 130 ml/hr., respectively; and nitrogen gas was fed under atmospheric pressure into the nozzle. From the exit of the die, there is obtained a strand having a hollow, an islands-in-sea structure wherein a ratio of the islands was 78% in the cross-section. The strand was drawn to obtain a multicore hollow optical fiber having an outside diameter of 0.93 mm and an inside diameter of 0.59 mm. A photomicrograph of the cross-section of the resultant multicore hollow optical fiber is shown in FIG. 6. The cross-section of the resultant multicore hollow optical fiber was carefully observed, and some parts contain disordered islands. However, they hardly affected the resultant fiber as a light guide. The fiber was capable of transmitting room light even when it was 15 meters in length. As a result, it was confirmed that the resultant fiber was advantageously used as a light guide for a short distance, i.e., a few meters.

The multicore hollow optical fiber was subjected to a tensile test. The measurement was conducted according to JIS C 6861. A sample was fixed to a tensile test machine by inserting 0.5 mm of a bare plastic optical fiber into the hollow of the sample. The sample was 100 mm and a tensile rate was 100 mm/min. The sample exibited a good mechanical strength, that is, a ratio of the breaking extension was 80 to 150%, and the breaking strength was 2.3 Kg per line.

Further, one meter of the multicore hollow optical fiber was cut out and connected to a light source. The light emmited from an end face of the cut fiber was projected on a piece of white paper. Photomicrographs were taken from the other side of the paper. FIGS. 7A to 7D shows light distributions in distances between the end of the multicore hollow optical fiber and the paper of 0 mm, 1 mm, 2 mm, and 3 mm, respectively. These figures indicate that this multicore hollow optical fiber was able to provide clear and uniform patterns of light.

Figure 8A:
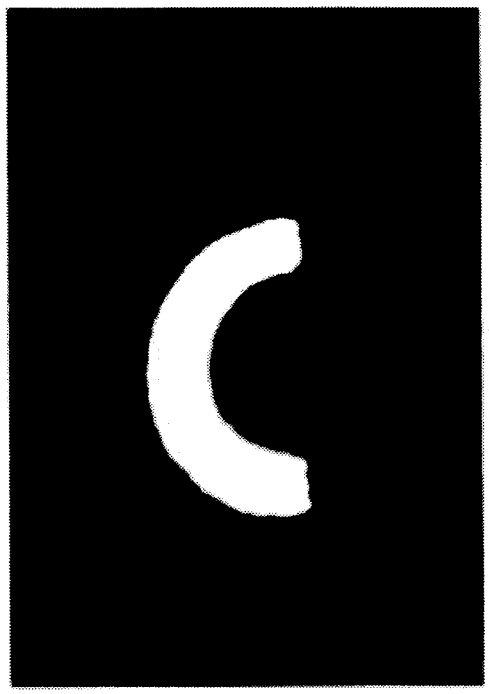
FIGS. 8A and 8B are photographs of light pattern given by a light guide composed of the multicore hollow optical fiber obtained in Example 3, whose half of the end face is covered with a black adhesive agent.
Figure 8B:
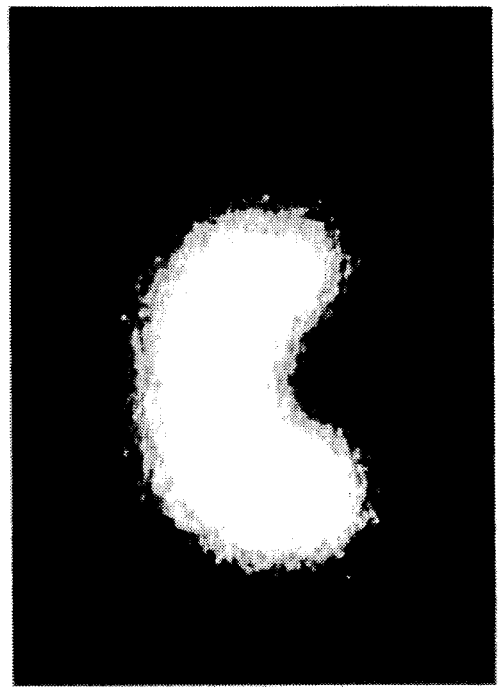
Figure 9A:
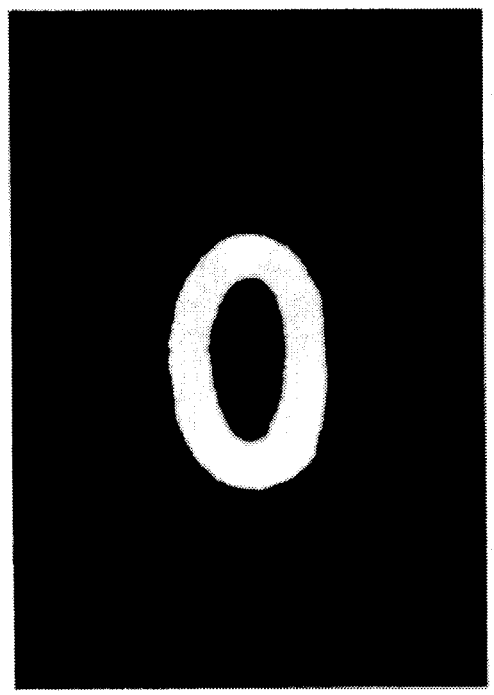
FIGS. 9A and 9B are photographs of light pattern given by a light guide composed of the multicore hollow optical fiber obtained in Example 3, whose end shape is changed.
Figure 9B:
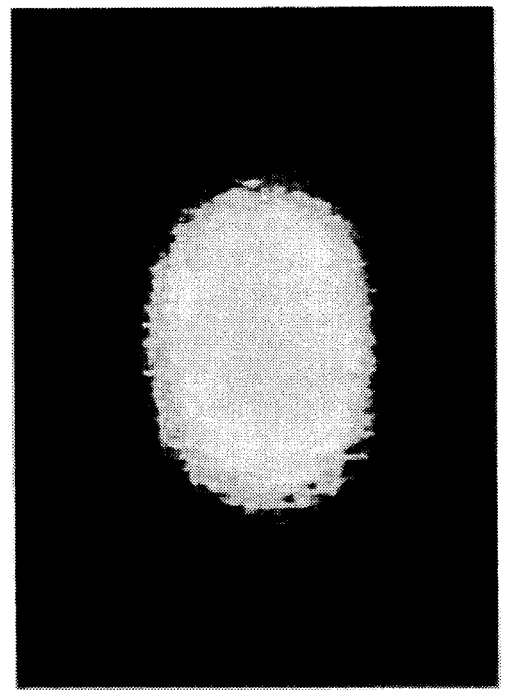

One meter of the obtained multicore hollow optical fiber was cut, and a half of the light-side end face of the cut fiber was covered with a black adhesive. The light emitted from the end face was projected to take photomicrographs in the same manner as FIGS. 7A to 7D. FIGS. 8A and 8B show light distributions in distances between the end of the multicore hollow optical fiber and the paper of 0 mm and 1 mm, respectively. Further, the end of the multicore hollow optical fiber was transformed to an oval and photomicrographs were taken in the same manner as FIGS. 8A and 8B. FIGS. 9A and 9B show light distributions in distances between the end of the multicore hollow optical fiber and the paper of 0 mm and 1 mm, respectively.

[EXAMPLE 4]

Figure 10:
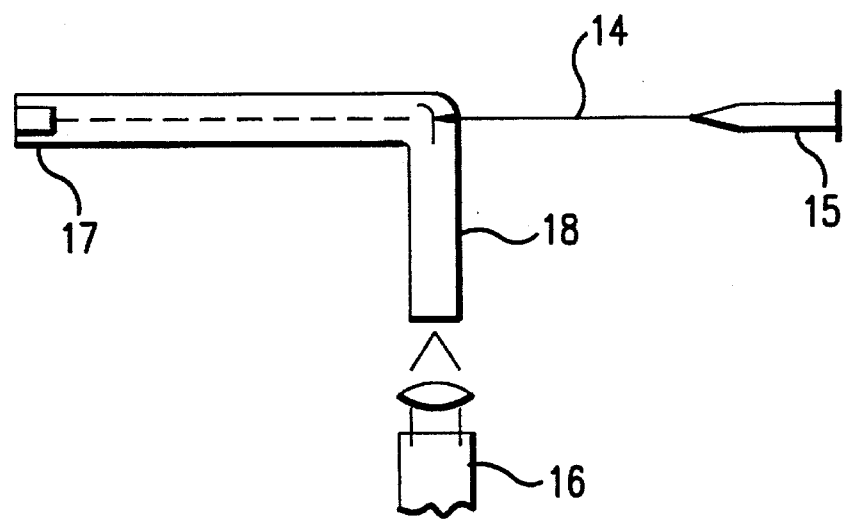
FIG. 10 is a schematic representation of an endoscope, which is composed of a multicore hollow optical fiber of the present invention.
Figure 11:
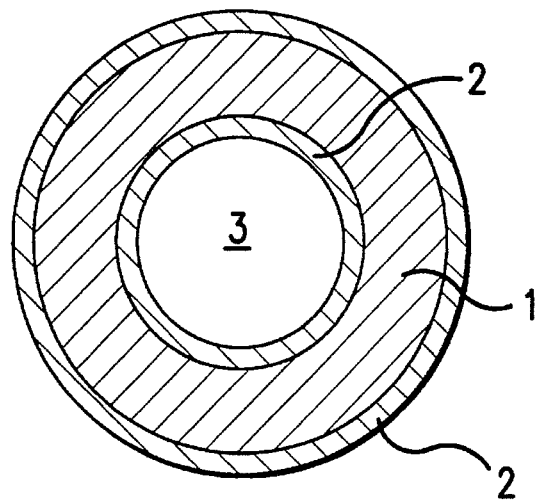
FIG. 11 is a cross-section view of a conventional optical fiber.
Figure 12:
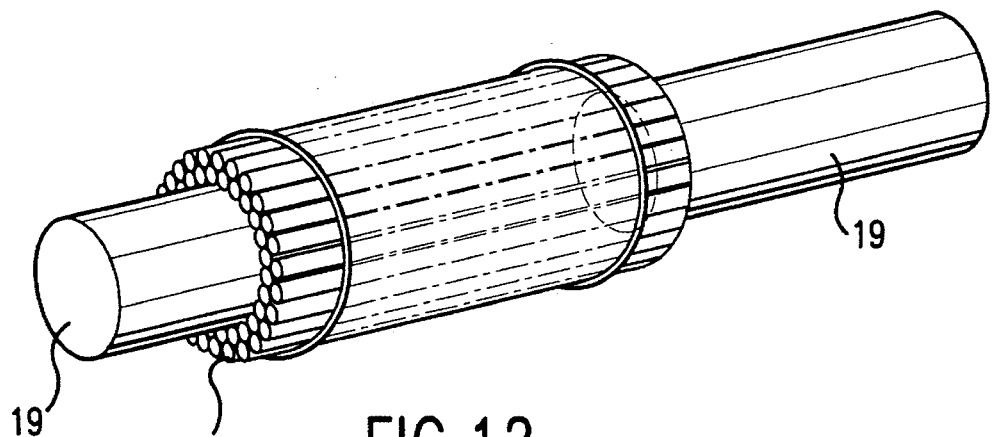
FIG. 12 is a fiber bundel in a conventional process for an optical fiber.
Figure 13:
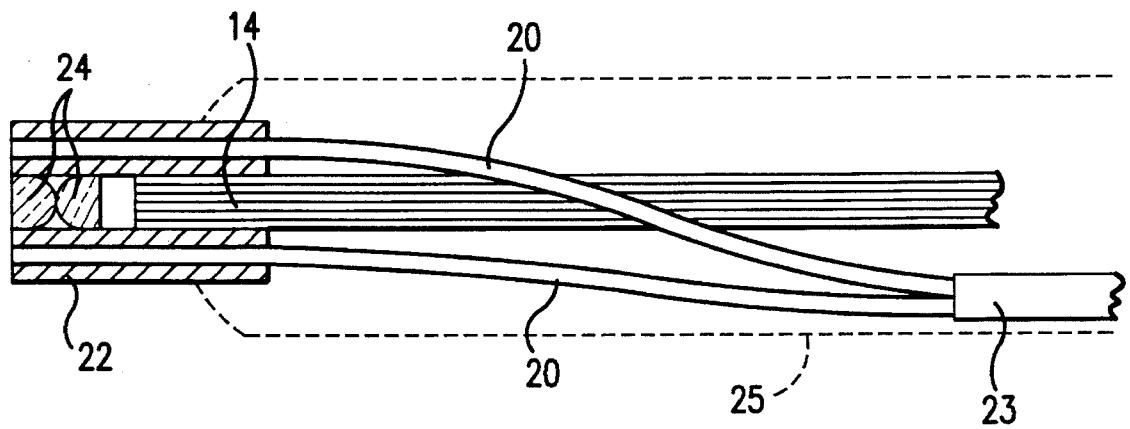
FIG. 13 is a cross-section view of a conventional endoscope.
Figure 14A:
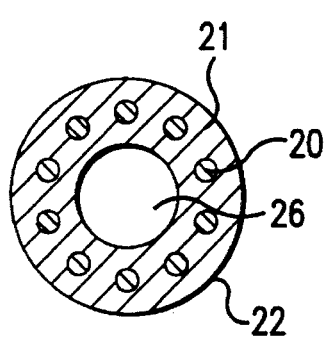
FIGS. 14A and 14B are a cross-section view and a longitudinal section view of a conventional endoscope, respectively.
Figure 14B:
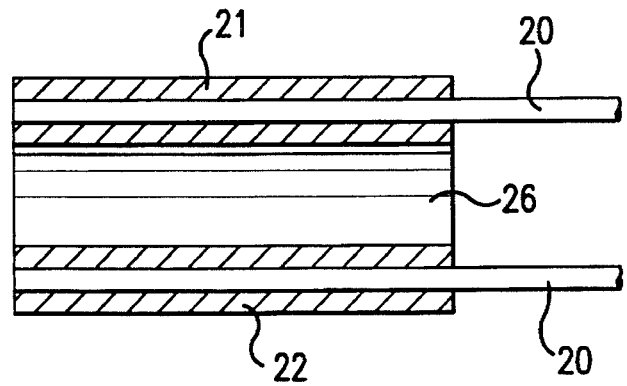

An endoscope as shown in FIG. 10 was prepared with the multicore hollow optical fiber prepared in Example 3. A 10-mm rift was formed along the axis of the fiber with a razor at a point of 30 cm apart from one end of one-meter multicore optical fiber 18. Then, a plastic image fiber having a diameter of 0.5 mm and 3,500 picture elements was inserted into the fiber from the rift. The image fiber was easily fitted to the hollow. The fiber did not break at the rift. SELFOC lens (trademark) as object lens 17 and eye lens 15 were fitted to the ends of the plastic image fiber, respectively, and then light was supplied from one end of multicore hollow optical fiber 14. By using the thus prepared endoscope, an object in a dark and small space was observed.

[EXAMPLE 5]

A multicore hollow optical fiber was produced in substantially the same manner as in Example 3, except that a resin having a ratio of vinylidene fluoride unit to tetrafluoroethylene unit of 85.5:14.5, a melt flow index of 40 g/10 min., and a refractive index of 1.40 was used as a cladding resin. The structure and function of the resulting multicore hollow optical fiber were almost equal to those of the fiber produced in Example 3.

INDUSTRIAL APPLICABILITY

There is provided a flexible multicore hollow optical fiber having a small aperture which is not broken by pressing or bending. This fiber used for a compact endoscope or the like can be provided by fitting an image fiber or the like in its hollow part.

What is claimed is:

1. A multicore hollow optical fiber comprising a hollow central part and a plastic peripheral part, wherein a cross-section of the peripheral part has (a) an islands-in-sea structure; (b) islands comprising a core resin having at least higher refractive index than a cladding resin; (c) a sea comprising the cladding resin or a third resin; (d) the core resin surrounded by the cladding resin; and (e) no substantial voids; and the multicore hollow optical fiber having, in the direction of the axis of the multicore hollow optical fiber, approximately the same cross-section of the peripheral part continuously from one end to the other end of the multicore hollow optical fiber.

2. The multicore hollow optical fiber according to claim 1, wherein the islands comprise the core resin and the sea comprises the cladding resin.

3. The multicore hollow optical fiber according to claim 1, wherein the islands comprise the core resin and the cladding resin surrounding the core resin and the sea comprises the third resin.

4. The multicore hollow optical fiber according to claim 1, wherein the area of the core resin area is 50 to 95% of that of the cross-section.

5. The multicore hollow optical fiber according to claim 1, wherein the number of the islands is 100 or more.

6. The multicore hollow optical fiber according to claim 1, wherein the cladding resin has a refractive index being smaller than that of the core resin by 0.02 or more.

7. The multicore hollow optical fiber according to claim 1, wherein the number of the islands in the direction of the radius of the cross-section is 2 or more.

8. The multicore hollow optical fiber according to claim 1, wherein the outside and inside diameters of the optical fiber are between 0.1 and 5.0 mm and between 0.05 and 4.0 mm, respectively.

9. A method for preparing a multicore hollow optical fiber, which comprises feeding a melted core resin having a higher refractive index than a cladding resin and a melted cladding resin in a composite spinning die; extruding the core resin from a die plate to form a linear core; extruding the cladding resin so as to surround the linear core to form an islands-in-sea structure wherein the core constitutes islands and the cladding constitutes a sea in a cross-section of the multicore hollow optical fiber; introducing fluid into a central part of the islands-in-sea structure to form a hollow; and drawing the islands-in-sea structure having the hollow to a desired diameter while cooling.

10. A method for preparing a multicore hollow optical fiber, which comprises feeding a melted core resin having a higher refractive index than a cladding resin, a melted cladding resin and a melted third resin in a composite a pinning die; extruding the core resin from a die plate to form a linear core; extruding the cladding resin so as to surround the linear core; extruding the melted third resin so as to surround the linear core which is surrounded by the cladding resin to form an islands-in-sea structure wherein the core and the cladding constitute islands and the third resin constitutes a sea in a cross-section of the multicore hollow optical fiber; introducing fluid into a central part of the islands-in-sea structure to form a hollow; and drawing the islands-in-sea structure having a hollow to a desired diameter while cooling.

* * * * *